(12) United States Patent
Ostroff et al.

(10) Patent No.: US 9,808,617 B2
(45) Date of Patent: Nov. 7, 2017

(54) X-RAY IDENTIFICATION FOR ACTIVE IMPLANTABLE MEDICAL DEVICE

(71) Applicant: Nanostim, Inc., Sunnyvale, CA (US)

(72) Inventors: Alan Ostroff, Pleasanton, CA (US); Paul Paspa, Los Gatos, CA (US); Peter M. Jacobson, Livermore, CA (US); Wade A. Keller, Aliso Viejo, CA (US); Christopher Alan Hubbard, Woodridge, IL (US)

(73) Assignee: Pacesetter, Inc., Sunnyvale, CA (US)

( * ) Notice: Subject to any disclaimer, the term of this patent is extended or adjusted under 35 U.S.C. 154(b) by 768 days.

(21) Appl. No.: 13/972,828

(22) Filed: Aug. 21, 2013

(65) Prior Publication Data

US 2014/0058494 A1 Feb. 27, 2014

Related U.S. Application Data

(60) Provisional application No. 61/691,721, filed on Aug. 21, 2012.

(51) Int. Cl.
*A61N 1/372* (2006.01)
*A61N 1/05* (2006.01)
*A61N 1/375* (2006.01)
*A61B 90/00* (2016.01)

(52) U.S. Cl.
CPC ......... *A61N 1/0587* (2013.01); *A61N 1/3756* (2013.01); *A61N 1/37205* (2013.01); *A61B 2090/3966* (2016.02); *A61N 1/0573* (2013.01)

(58) Field of Classification Search
CPC ........ A61N 1/05; A61N 1/086; A61N 1/0573; A61N 1/0601; A61N 1/0587; A61N 1/3756

USPC .......................................................... 607/122
See application file for complete search history.

(56) References Cited

U.S. PATENT DOCUMENTS

| | | |
|---|---|---|
| 2003/0204233 A1 | 10/2003 | Laske et al. |
| 2005/0021108 A1 | 1/2005 | Klosterman et al. |
| 2005/0192620 A1 | 9/2005 | Cully et al. |
| 2010/0305629 A1 | 12/2010 | Lund et al. |

(Continued)

FOREIGN PATENT DOCUMENTS

| | | |
|---|---|---|
| WO | 02/32500 A2 | 4/2002 |
| WO | 2007/047681 A2 | 4/2007 |
| WO | 2008/133553 A2 | 11/2008 |

OTHER PUBLICATIONS

International Search Report WO dated Nov. 15, 2013; Related Serial No. PCT/US2013/055986.

(Continued)

*Primary Examiner* — Niketa Patel
*Assistant Examiner* — Minh Duc Pham
(74) *Attorney, Agent, or Firm* — Theresa A. Raymer

(57) ABSTRACT

An active implantable medical device is disclosed herein having a radio-opaque marker. The radio-opaque marker can be formed within an exterior wall of the device or within recesses on the outside of the exterior wall. The implantable medical device can be a leadless pacemaker. The shape of the radio-opaque marker can be designed to facilitate visualization and identification of the location, orientation, and rotation of the implanted medical device by conventional fluoroscopy. Methods of use are also disclosed.

21 Claims, 5 Drawing Sheets

(56) References Cited

U.S. PATENT DOCUMENTS

| | | | |
|---|---|---|---|
| 2011/0125240 A1* | 5/2011 | Zhao | A61N 1/0573 |
| | | | 607/116 |
| 2011/0190842 A1 | 8/2011 | Johnson et al. | |
| 2012/0107672 A1 | 5/2012 | Zhao et al. | |
| 2012/0109236 A1 | 5/2012 | Jacobson et al. | |
| 2012/0158111 A1 | 6/2012 | Khairkhahan et al. | |
| 2012/0290021 A1* | 11/2012 | Saurkar | A61N 1/37205 |
| | | | 607/2 |
| 2013/0150915 A1* | 6/2013 | Kane | A61N 1/375 |
| | | | 607/36 |

OTHER PUBLICATIONS

Notification Concerning Transmittal of International Preliminary Report on Patentability, dated Mar. 5, 2015; Related Serial No. PCT/US2013/055986.

Supplementary European Search Report dated Mar. 18, 2016; Related Serial No. 13831621.1.

\* cited by examiner

X-RAY IDENTIFICATION FOR ACTIVE IMPLANTABLE MEDICAL DEVICE

CROSS-REFERENCE TO RELATED APPLICATIONS

This application claims the benefit of U.S. Provisional Application No. 61/691,721, filed on Aug. 21, 2012, titled "X-Ray Identification for Active Implantable Medical Device", the contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to implantable medical devices and more particularly to implantable leadless cardiac pacemakers.

BACKGROUND

Radiographic identification has been useful in helping clinicians identify in-vivo active implantable medical devices, such as implantable cardiac pacemakers. Typically, identification occurs via X-ray illumination to observe a radio-opaque tag or marker located inside the electronic compartment or embedded in the header of the active implantable device.

Radiographic identification of implantable medical devices has become more challenging because of the reduction in volume and size of implantable medical devices. The reduction in size of implantable medical devices makes it more challenging to find acceptable locations for placing radiographic tags that can be identified and visualized using standard medical radiographic equipment.

SUMMARY OF THE DISCLOSURE

An implantable medical device comprising a cell, and a radio-opaque marker integrated into the cell.

In some embodiments, the radio-opaque marker is located inside the cell. In other embodiments, the radio-opaque marker is embedded in an exterior surface of the cell.

In one embodiment, the radio-opaque marker comprises tungsten, tantalum, platinum, gold, or other radio-opaque materials.

In some embodiments, the implantable medical device is a leadless pacemaker.

A method for identifying an implantable device is provided, comprising marking a portion of a cell of the implantable device with a radio-opaque marker.

In some embodiments, the radio-opaque marker comprises one or more of tungsten, tantalum, platinum, or gold, or other radio-opaque materials.

In another embodiment, the marked portion of the implantable medical device is relatively opaque to X-ray radiation.

In some embodiments, the radio-opaque marker is located within the cell of the implantable device.

In some embodiments, forming the radio-opaque marker in a desired shape comprises patterning, laser cutting, wire cutting, chemical machining, stamping, or mechanical machining prior to marking.

In some embodiments, the method further comprises forming recesses in an exterior surface of the cell, wherein the radio-opaque marker is deposited in the recesses on the exterior surface of the cell.

In some embodiments, the method further comprises treating the exterior surface of the cell after depositing the radio-opaque marker to smooth the exterior surface of the cell.

In one embodiment, marking comprises inserting a radio-opaque marker within the cell of the implantable device.

A leadless pacemaker for pacing a heart of a human is provided, comprising a cell, and a radio-opaque marker integrated into the cell.

In some embodiments, the radio-opaque marker is contained within an interior portion of the cell.

In another embodiment, the radio-opaque marker is embedded in an exterior surface of the cell.

In some embodiments, the radio-opaque marker comprises tungsten, tantalum, platinum, gold, or other radio-opaque materials.

In another embodiment, the radio-opaque marker is shaped to indicate the rotation of the pacemaker when scanned by X-ray radiation.

In some embodiments, the radio-opaque marker comprises a plurality of markers.

A leadless cardiac pacemaker is provided, comprising an electronics housing, pacing electronics disposed in the electronics housing, a tip electrode electrically coupled to the pacing electronics, a cell housing, an energy source disposed in the cell housing and electrically coupled to the pacing electronics, and a radio-opaque marker integrated into a wall of the cell housing.

In one embodiment, the radio-opaque marker comprises multiple discrete markings.

A leadless cardiac pacemaker is further provided, comprising an electronics housing, pacing electronics disposed in the electronics housing, a tip electrode electrically coupled to the pacing electronics, a cell housing, an energy source disposed in the cell housing and electrically coupled to the pacing electronics, and a radio-opaque marker contained within cell housing.

In some embodiments, the radio-opaque marker is disposed between an interior side of the cell housing and an anode of the energy source.

In another embodiment, the pacemaker further comprises a thermal separator disposed between the anode and a cathode of the energy source.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
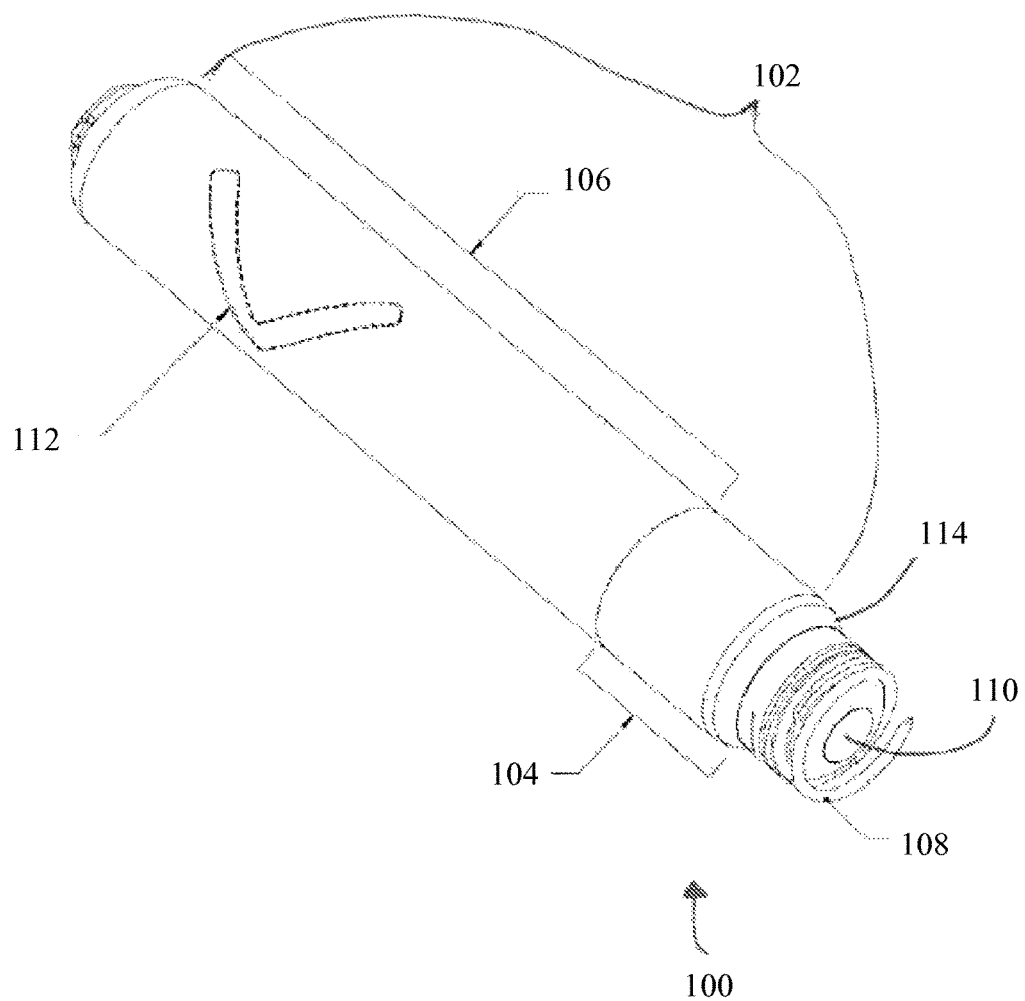
FIG. 1A illustrates a leadless cardiac pacemaker.

Technological advances have allowed for a reduction in the size of active implantable medical devices. Decreasing the size of the implantable medical devices has made it more challenging to find acceptable locations for placing radiographic markers or tags on the active medical device. Radiographic visualization of the implantable medical device can be more difficult because of limits with conventional X-ray machines and the orientation of the body of the patient with respect to conventional X-ray machines.

Active implantable medical devices typically have an electronics compartment and a cell. The radiographic or radio-opaque marker or tag is usually placed inside the electronics compartment. However, the electronics compartment has radio-opaque components such as tantalum capacitors. The radio-opaque tag or marker can be shadowed, obscured, or confused with the neighboring radio-opaque materials using conventional fluoroscopy methods. The components of the electronics compartment can produce visual noise and obstruct clear visualization of the radio-opaque marker.

The use of markers can also complicate the design of the electronics compartment. Radio-opaque markers are commonly made using electrically conductive materials that further limit the acceptable locations for the marker because of the risk of shorting electrically active surfaces inside the electronics compartment.

In some implantable active medical devices the volume of the electronics compartment is on the order of about 0.25 cc and contains several tantalum capacitors. The small volume and electrical components of the electronics compartment can make placement of the radio-opaque marker difficult to accurately visualize using conventional fluoroscopy.

Placing a radio-opaque marker outside of the exterior wall of the implantable medical device is not an option in many applications. Many implantable medical devices are optimized for delivery through a catheter and are isodiametric. Active medical devices implanted using catheters are typically optimized to have the smallest diameter in order to facilitate passing the implantable device into the vasculature. Adding a radio-opaque marker or tag to the exterior wall of the implantable device can unnecessarily increase the overall diameter of the device or create an elevated surface that could interfere with delivery and retrieval of the device. Furthermore, the presence of a radio-opaque marker on the exterior surface of the implantable device may disrupt the blood flow surrounding the implant and lead to unnecessary fibrosis complicating implant retrieval.

In addition to locating a radio-opaque marker inside the electronics compartment, manufacturers have placed radio-opaque markers inside the insulating header of the active implantable device. However, for many active implantable device applications, such as in leadless cardiac pacemakers, the surface area and volume available in the header are insufficient and often obscured by platinum electrodes and wires, and other radio-opaque materials in or adjacent to the header.

Improved visualization and resolution of the implantable medical device is also desired. Increased precision in the visualization of the direction and magnitude of rotation of the active implantable medical device can facilitate the fixation and retrieval of the device and decrease the likelihood of complications and mistakes during fixation and retrieval.

Multiple solutions for improved radiographic visualization of the implantable medical device are disclosed herein, including placing a radio-opaque marker within or on the exterior of a cell component of an implantable medical device. In some embodiments, the radio-opaque marker can be placed within the wall of the cell. In other embodiments, the radio-opaque marker can also be placed on the exterior wall of the cell within a recess shaped to receive the radio-opaque marker.

The disclosure in the present application is applicable to implantable active medical devices in general. The examples discussed in greater detail below illustrate embodiments of implantable active medical devices that are leadless cardiac pacemakers.

The cell or energy source (e.g., battery) compartment in an implantable medical device is typically a few times larger than the volume of the electronics component of the device. For example, in leadless cardiac pacemakers the cell is approximately three times the volume of the electronics compartment. The larger size of the cell provides additional surface area to apply a radio-opaque marker.

Typically, the cell compartment contains materials that are less radiographically dense than the materials present in the electronics component. The cell compartment can include materials such as lithium, carbon, titanium, electrolyte, and other materials commonly found in primary lithium cell designs. The materials in the cell battery produce less of a radiographic response and less background noise than the materials in the electronics component. For example, lithium, carbon, titanium, and electrolyte appear nearly transparent on fluoroscopy when compared to the noise produced by the tantalum capacitors in the electronics cell.

The radio-opaque marking on the cell compartment can also improve the radiographic visualization and identification of the direction and magnitude of rotation of the implantable device. Improved visualization of the implantable device can make fixation and retrieval easier and less risky for patients.

FIG. 1A shows an implantable medical device illustrated as a leadless cardiac pacemaker 100. The leadless pacemaker 100 has a hermetic housing 102. The hermetic housing 102 comprises an electronics compartment 104 and cell 106. The cardiac pacemaker 100 includes a helix 108 used to attach the device to the desired tissue area. An electrode 110 disposed near a distal portion of the hermetic housing can be used to stimulate the tissue. The cell 106 shows the location profile of the radio-opaque marker 112 inside the cell 106. The leadless pacemaker 100 includes a header assembly 114 adjacent to the electronics compartment.

In the embodiment of FIG. 1A, the cell can be connected to pacing electronics within the electronics compartment 104. The pacing electronics can also be connected to the electrode 110. With this configuration, the electrode 110 can be used as the stimulation electrode and the housing of the cell can be used as a ring or can electrode for the pacemaker. This configuration does not to require an additional pacemaker housing and/or ring electrode around the cell, which can significantly reduce the size and cost of the pacemaker.

Header assembly 114 can be configured to electrically isolate electrode 110 from the rest of the device, including from the electronics and the cell housing. The header assembly can include a ceramic to metal feedthrough or a glass to metal feedthrough to connect the tip electrode to the pacing electronics in the electronics compartment, as known in the art. The electrode 110 can be, for example, a raised or "button" shaped electrode disposed on a distal tip of the housing. The tip electrode can be other shapes, including square, rectangular, circular, flat, pointed, or otherwise shaped as known in the art. In additional embodiments, the electrode can be integrated into the helix 108.

When the pacemaker of FIG. 1A is activated, stimulation current can flow from the cell 106, at positive polarity during the stimulation pulse, to tip electrode 110, at negative polarity during the stimulation pulse. Consequently the cell 106 also serves as the positive ring electrode during stimulation. Header assembly separates the cell housing (acting as a ring or can electrode) from the tip electrode 110, both physically and electrically during use. In order for the pacemaker 100 of FIG. 1A to function properly when implanted in a heart of a patient, the tip electrode 110 must be driven negative with respect to the ring or can electrode (e.g., cell housing 106).

Figure 1B:
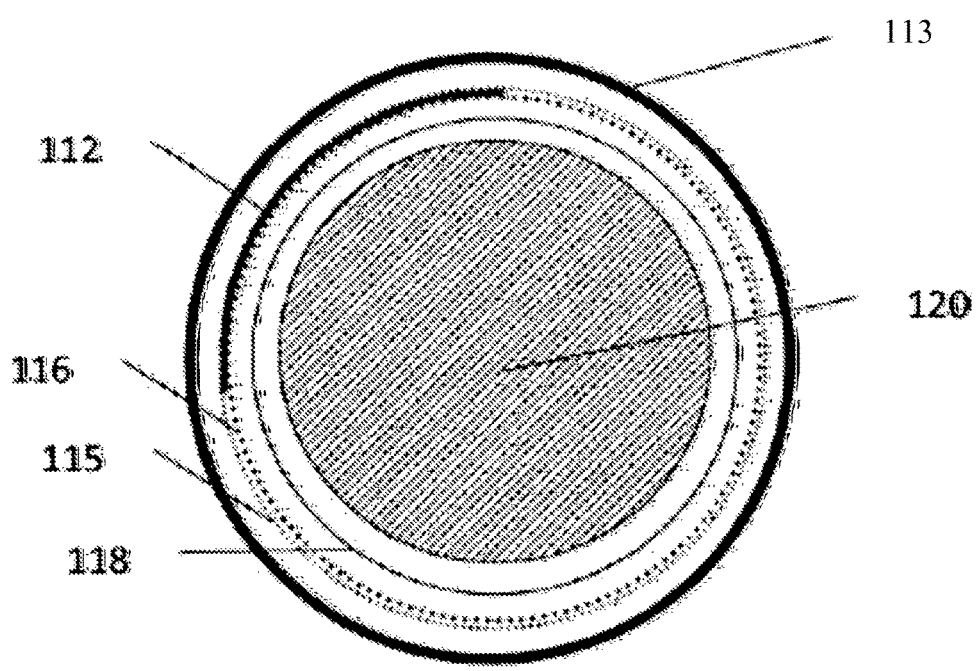
FIG. 1B is a cross section of the leadless cardiac pacemaker illustrated in FIG. 1A.

FIG. 1B illustrates a cross-section of an area of the cell 106. The cell 106 includes a hermetic wall 113 on the exterior. The hermetic wall 113 has an exterior side and interior side 115. The cell 106 can also have an anode 116 contacting an interior side 115 of the hermetic wall. A thermal separator 118 can insulate the anode 116 from a cathode/current collector 120. The cell can be filled with an electrolyte. The radio-opaque marker 112 is illustrated between the interior side 115 of the hermetic wall and the anode 116. The skilled artisan will appreciate that the figures are not necessarily to scale. FIG. 1B is illustrated with a small space between the interior side of the hermetic wall 115 and the anode 116 to show the positioning of the marker 112 between the interior of wall 115 and anode 116. The interior of the wall 116 can abut or contact the anode 116 in areas where the marker is not present.

Figure 2A:
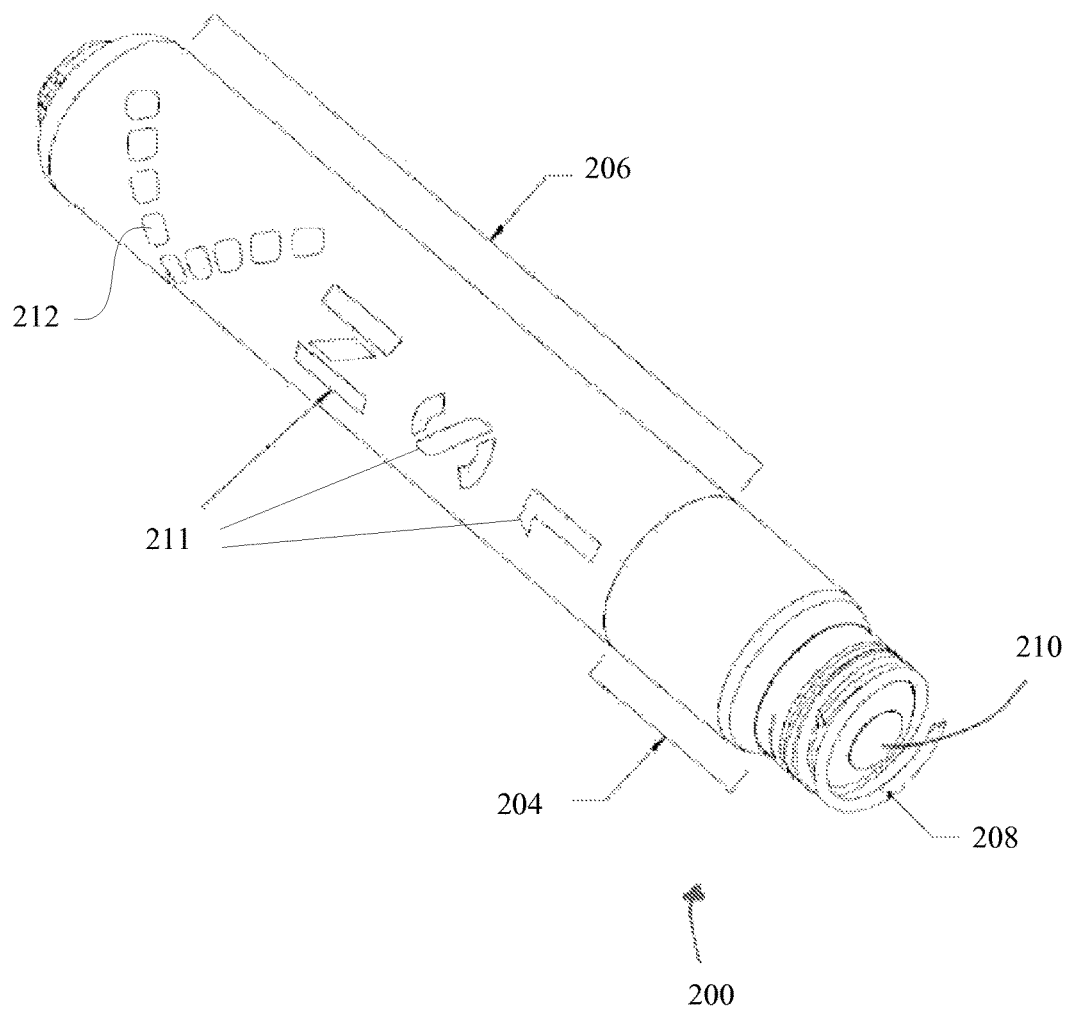
FIG. 2A illustrates a leadless cardiac pacemaker in accordance with another embodiment.
Figure 2B:
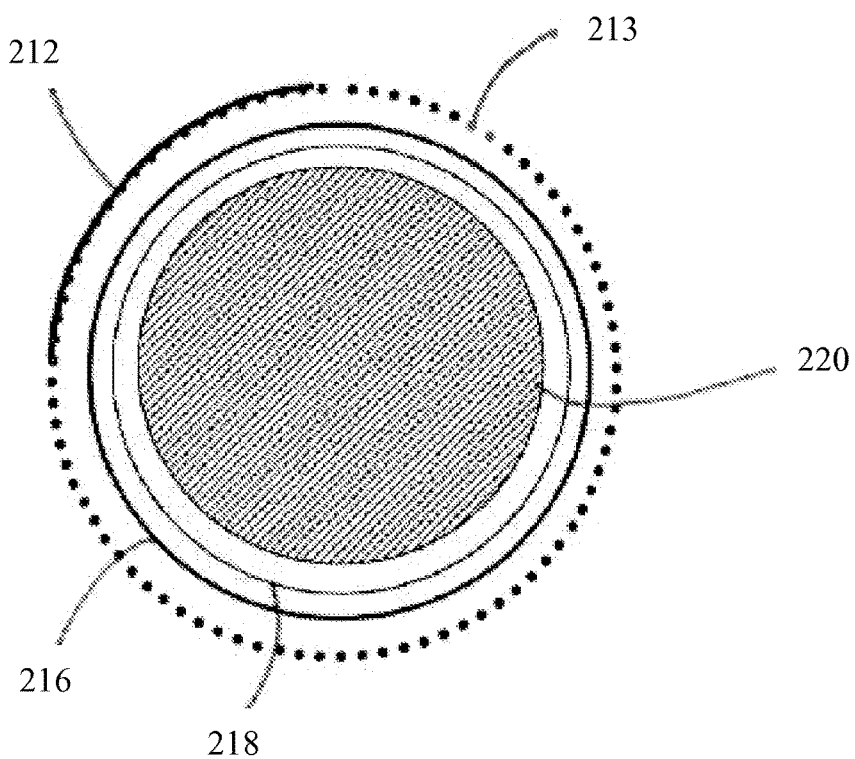
FIG. 2B is a cross section of the leadless cardiac pacemaker illustrated in FIG. 2A.

In some embodiments the radio-opaque marker can be formed within the hermetic wall. In some embodiments the radio-opaque marker can be formed in depressions on the interior of the hermetic wall. In some embodiments the radio-opaque marker can be formed in depressions on the exterior of the hermetic wall, as illustrated in FIGS. 2A-2B and discussed below. The radio-opaque markers described herein can be made out of a material that can be identified by fluoroscopy. Examples of materials include tantalum, tungsten, platinum, gold, or other radio-opaque alloys.

The radio-opaque marker can be formed in a variety of shapes. The shape of the radio-opaque marker can be designed to facilitate identification of the location and rotation of the medical device using conventional X-ray identification methods. In some embodiments the radio-opaque marker can be any letter of the alphabet. In some embodiments the radio-opaque marker can be a geometric shape, such as a polygon. In some embodiments the radio opaque marker can be in the shape of an arrow or tip of an arrow. In some embodiments the radio-opaque marker can be a non-symmetrical shape.

The radio-opaque marker can have a thickness selected to be visible via fluoroscopy. In some embodiments the thickness of the radio-opaque marker can be about 0.01 inches or less. In some embodiments the thickness of the radio-opaque marker can be about 0.001 inches to about 0.01 inches. In some embodiments the thickness of the radio-opaque marker can be about 0.004 inches.

The radio-opaque marker for implanting within the cell can be manufactured using a variety of processes including but not limited to laser cutting, wire EDM cutting, chemical machining, stamping or mechanical machining. The edges of the marker can be softened, dulled, or broken from stamping, electropolishing, rolling, tumbling, or harparizing to reduce the likelihood that the edges of the marker will damage the battery by piercing the anode and breaking through the internal thermal separator of the cell.

In some embodiments the radio-opaque marker can be formed on the exterior of the cell wall. For example, the radio-opaque marker can be formed in depressions on the exterior of the cell wall. The radio-opaque marker can be inlayed in the exterior of the cell wall without changing the diameter of the cell wall, symmetry of the implantable device, or creating any protrusions in the cell wall. The implantable medical device is preferably isodiametric. It is desirable for the implantable medical device to be isodiametric and minimize the diameter in order to facilitate catheter delivery.

FIG. 2A shows an implantable medical device illustrated as a leadless cardiac pacemaker 200. The leadless cardiac pacemaker 200 includes an electronics compartment 204 and cell 206. The cardiac pacemaker 200 includes a helix 208 used to attach the device to the desired tissue area. An electrode 210 can be used to stimulate the tissue. The cell 206 shows the location of the radio-opaque marker 212 integrally formed with the exterior of the cell 206. The cell 206 also includes ID tag 211 integrally formed in depressions in the exterior of the cell 206.

In some embodiments, the radio-opaque marker can be a continuous shape. In some embodiments, the radio-opaque marker can be a non-continuous shape or can include multiple discrete markers. FIG. 2A illustrates a radio-opaque marker 212 with multiple dots or marks in the shape of an arrow tip. FIG. 2A also illustrates an ID tag 211 with multiple separate discrete shapes and letters.

FIG. 2B illustrates a cross-section of an area of the cell 206 from FIG. 2A. The cell 206 includes a hermetic wall 213 on the exterior. The cell 206 has an anode 216 contacting an interior side of the hermetic wall 213. A thermal separator 218 insulates the anode 216 from a cathode/current collector 220. The cell can also be filled with electrolyte. The radio-opaque marker 212 is illustrated in FIG. 2B as integrally formed within depressions in the exterior of the hermetic wall 213.

The depression(s) in the exterior of the cell wall can be arranged to form the desired shape for the radio-opaque marker. The depressions can form a continuous or discontinuous shape for the radio-opaque marker. The use of multiple discrete depressions can allow for greater mechanical integrity in the cell wall because less material is removed from the cell wall. The depressions in the cell wall can be created by mechanical machining, stamping, chemical etching, or other suitable means.

Radio-opaque materials such as tungsten, platinum, gold, tantalum, or other radio-opaque materials can be formed in the depressions by deposition, plating, cladding, printing, inlay, or other suitable deposition means. In some embodiments a mask may be used to facilitate the formation of the radio-opaque material in the depressions.

In some embodiments an additional processing step can be used to process the exterior surface of the cell after forming the radio-opaque material in the depressions. For example, a processing step such as grinding or polishing may be used to obtain a smooth surface finish and/or remove radio-opaque material from areas outside of the depressions.

In some embodiments the cell can be coated with a thin layer to provide a uniform finish on the cell. The finishing material and thickness can be selected such that it does not alter the X-ray image of the implantable medical device. For example, the thin finishing coating could have a thickness of less than about 0.001 inches.

The thickness of the depressions and the radio-opaque marker formed in the depressions can be up to about 90% of the thickness of the cell wall. Typically the cell wall thickness used in some implantable medical devices can be around 0.01 inches. In some embodiments the depressions can have a thickness or depth marker can be about 0.001 inches to about 0.01 inches. The depressions can have an exemplary thickness or depth of about 0.004 inches.

Figure 3:
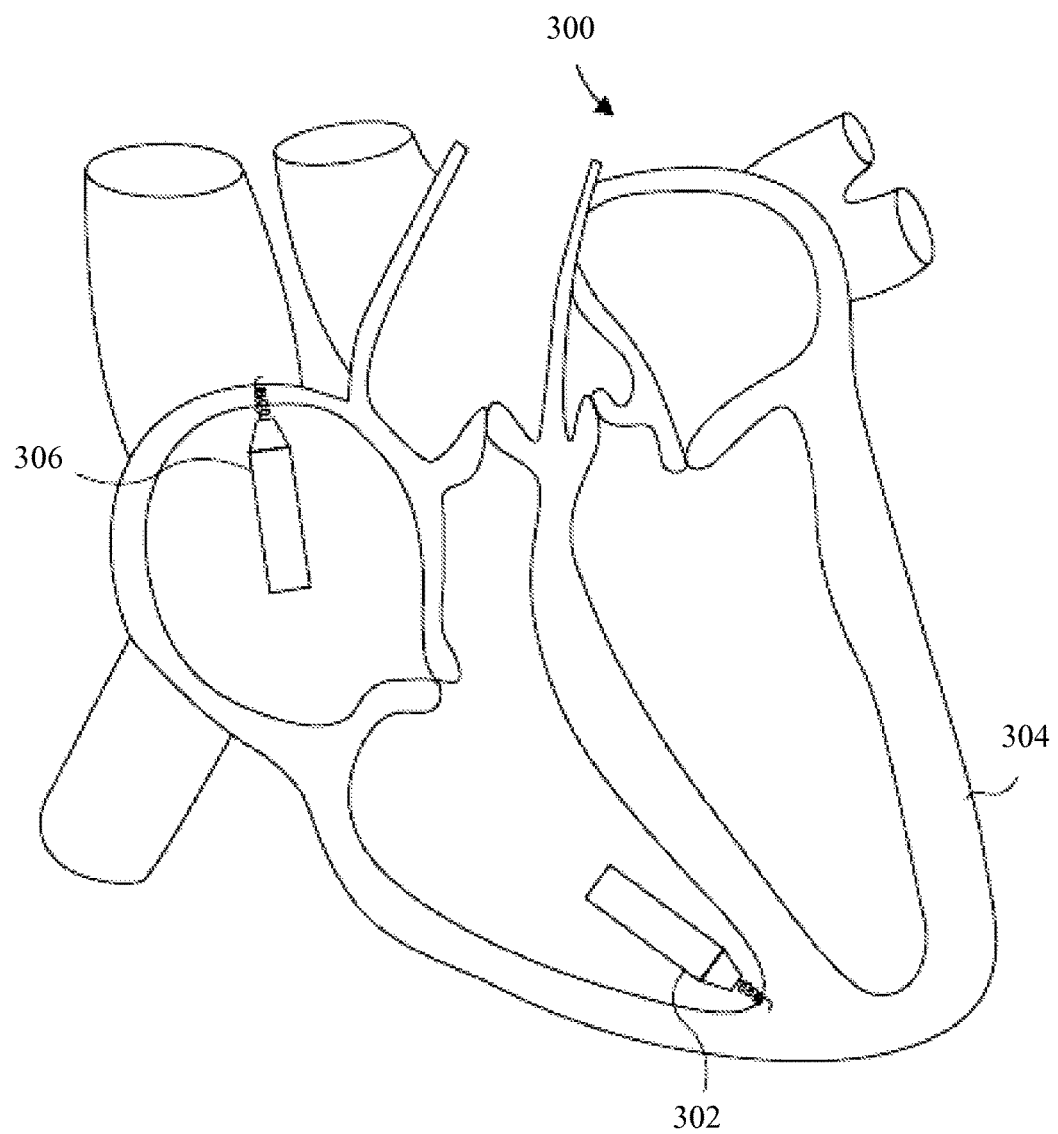
FIG. 3 is a pictorial diagram showing an embodiment of a cardiac pacing system that includes a leadless cardiac pacemaker.

FIG. 3 shows an example of leadless cardiac pacemakers 302 and 306 attached to the cardiac wall 304 of the heart 300. U.S. application Ser. No. 13/324,802 filed on Dec. 13, 2011, and Ser. No. 13/331,922 filed on Dec. 20, 2011, disclose leadless cardiac pacemakers and methods for implanting and removing leadless pacemakers, both are incorporated by reference herein in their entirety.

The implantable medical devices and methods for marking implantable medical devices disclosed herein result in improved radiographic identification of the location, orientation, and rotation of the implanted device. The improved radiographic identification makes implanting, repositioning and removing the devices in the patient more efficient, easier, and less risky for the patient. The improvements in marking the implantable medical device allow for further decreases in the overall size of the implantable medical device.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. The present invention descriptions are intended to cover such alternatives, modifications, and equivalents as may be included within the spirit and scope of the invention as defined by the appended claims and otherwise appreciated by one of ordinary skill in the art.

What is claimed is:

1. An implantable medical device comprising:
   a battery, wherein the battery comprises:
      a battery housing comprising an exterior side and an interior side, and
      an energy source disposed in the battery housing; and
   a radio-opaque marker integrated into the battery, wherein the radio-opaque marker is located inside the battery, and wherein the radio-opaque marker is disposed between the interior side of the battery housing and the energy source.

2. The implantable medical device of claim 1, wherein the radio-opaque marker comprises tantalum.

3. The implantable medical device of claim 1, wherein the implantable medical device is a leadless pacemaker configured to be implanted within the heart of a human.

4. The implantable medical device of claim 1, wherein the battery housing is not surrounded by or enclosed in a separate housing.

5. The implantable medical device of claim 1, wherein the radio-opaque marker has a thickness of about 0.001 inches to about 0.01 inches.

6. The implantable medical device of claim 1, wherein the radio-opaque marker is in contact with the energy source.

7. A method for identifying an implantable device comprising: marking a portion of a battery of the implantable device with a radio-opaque marker, wherein the battery comprises a battery housing and an energy source disposed in the battery housing, wherein the battery housing comprises an exterior side and an interior side, and wherein the radio-opaque marker is located between the interior side of the battery housing and the energy source.

8. The method of claim 7, wherein the radio-opaque marker comprises tantalum.

9. A leadless pacemaker configured to be implanted within a heart of a human for pacing the heart, the leadless pacemaker comprising:
   a battery comprising a battery housing and an energy source disposed in the battery housing, wherein the battery housing comprises an exterior side and an interior side; and
   a radio-opaque marker disposed between the interior side of the battery housing and the energy source.

10. The leadless pacemaker of claim 9, wherein the radio-opaque marker is in contact with the energy source.

11. The leadless pacemaker of claim 9, wherein the radio-opaque marker comprises tantalum.

12. The leadless pacemaker of claim 9, wherein the radio-opaque marker comprises a plurality of markers.

13. A leadless cardiac pacemaker, comprising:
   an electronics housing;
   pacing electronics disposed in the electronics housing;
   a tip electrode electrically coupled to the pacing electronics;
   a battery comprising a battery housing, wherein the battery is electrically coupled to the pacing electronics, and wherein the battery housing comprises an exterior side and an interior side; and
   a radio-opaque marker disposed between the interior side of the battery housing and the energy source, wherein the battery housing is not surrounded by or enclosed in a separate housing.

14. The leadless cardiac pacemaker of claim 13, wherein the radio-opaque marker is disposed between an interior side of the battery housing and an anode of the energy source.

15. The leadless cardiac pacemaker of claim 14, further comprising a thermal separator disposed between the anode and a cathode of the energy source, wherein the radio-opaque marker comprises dull edges such as to prevent the edges of the marker from piercing the anode and breaking through the thermal separator.

16. The leadless cardiac pacemaker of claim 13, wherein the radio-opaque marker is shaped to indicate the rotation of the leadless pacemaker when scanned by X-ray radiation and wherein the radio-opaque marker is disposed between the interior side of the battery housing and the energy source such that it does not create an elevated surface on the exterior of the leadless pacemaker.

17. The leadless cardiac pacemaker of claim 13, wherein the radio-opaque marker has a thickness of about 0.001 inches to about 0.01 inches.

18. The leadless cardiac pacemaker of claim 13, wherein the radio-opaque marker is in contact with the energy source.

19. The leadless cardiac pacemaker of claim 18, wherein the radio-opaque marker comprises tantalum.

20. An implantable medical device configured to for delivery through a catheter and passage into vasculature, comprising:
- a battery comprising a battery housing and an energy source disposed in the battery housing; and
- a radio-opaque marker integrated into the battery, wherein:
  - the battery housing comprises an exterior side and an interior side, and
  - the radio-opaque marker is disposed between the interior side of the battery housing and the energy source.

21. The implantable medical device of claim 20, wherein the battery housing is not surrounded by or enclosed in a separate housing.

* * * * *